(12) United States Patent
Corbeil et al.

(10) Patent No.: US 7,028,707 B2
(45) Date of Patent: Apr. 18, 2006

(54) VALVE FOR USE WITH CHEST DRAINAGE SYSTEM

(75) Inventors: Scott E. Corbeil, Litchfield, NH (US);
Theodore Karwoski, Hollis, NH (US);
Nicholas Want, Manchester, NH (US);
Stephen J. Forcucci, Medford, MA (US)

(73) Assignee: Atrium Medical Corporation, Hudson, NH (US)

( * ) Notice: Subject to any disclaimer, the term of this patent is extended or adjusted under 35 U.S.C. 154(b) by 26 days.

(21) Appl. No.: 10/731,549

(22) Filed: Dec. 9, 2003

(65) Prior Publication Data

US 2005/0121081 A1 Jun. 9, 2005

(51) Int. Cl.
*F16K 17/18* (2006.01)
(52) U.S. Cl. ................. 137/493; 137/846; 604/317
(58) Field of Classification Search ............. 137/493, 137/844, 846; 604/317
See application file for complete search history.

(56) References Cited

U.S. PATENT DOCUMENTS

| | | | |
|---|---|---|---|
| 3,324,877 A * | 6/1967 | Bochan ............... | 137/512.15 |
| 3,504,699 A * | 4/1970 | Grise ................... | 137/846 |
| 4,747,844 A * | 5/1988 | Elliott ................. | 604/319 |
| 5,188,140 A * | 2/1993 | Kosaka ............... | 137/12 |
| 6,210,383 B1 * | 4/2001 | Want et al. .......... | 604/318 |
| 6,358,218 B1 * | 3/2002 | Want et al. .......... | 600/573 |

* cited by examiner

Primary Examiner—Stephen M. Hepperle
(74) Attorney, Agent, or Firm—Wilmer Cutler Pickering Hale and Dorr LLP

(57) ABSTRACT

A valve for use in a chest drainage device is disclosed, the chest drainage device is adapted to receive liquid and air from a patient's chest cavity via an inlet and to permit air to escape through an outlet for air to leave the chest drain, the inlet and outlet define a flow path and the valve is disposed along the flow path. The valve has a valve element that separates an upstream chamber from a downstream chamber and has a first and second sealing surface that are opposed so that when the first and second sealing surfaces are in contact, air pressure below a predetermined value will be prevented from moving from the downstream location to the upstream location. The valve element allows air to move from the upstream chamber to the downstream chamber at a low pressure differential. A pressure relief actuating element is disposed in the valve and located adjacent the valve element such that when the predetermined sub-atmospheric pressure limit between the upstream side and the downstream side is reached or exceeded, the valve element deforms and contacts the pressure relief actuating element such that the post causes the first and second sealing surfaces to partially separate and reduce the pressure differential.

34 Claims, 9 Drawing Sheets

VALVE FOR USE WITH CHEST DRAINAGE SYSTEM

BACKGROUND OF THE INVENTION

1. Field of the Invention

The present invention relates generally to a valve that is used to regulate the flow of fluid. In one particular application, the invention relates to a valve that is used in systems designed to drain fluid from the thoracic cavity.

2. Description of the Related Art

A number of fluid recovery systems have been developed for withdrawing fluid, such as air and/or blood, from a person after chest surgery or trauma. Such systems are intended to remove fluid from the pleural space or the mediastinal cavity and restore the vacuum (sub-atmospheric pressure) that is normally present in the pleural space. The systems are usually adapted to allow suction to be applied to the chest cavity to facilitate, among other things, the removal of the blood from the pleural space. Once the fluid has been removed, the pleural membrane is allowed to heal and the normal condition of the pleural space is restored.

Various drainage devices, of varying complexity, have been developed for the above-mentioned purpose of draining fluids from either the pleural or mediastinal space. These devices typically include a housing that contains a number of chambers to collect fluid from the pleural space. In addition to the chambers, the housing contains a number of components such as valves and ports that may be manufactured separately and then attached to the housing. Typical drainage devices must accomplish drainage by allowing air to flow from the chest and through the chest drain without allowing air to flow back into the chest cavity. Second, there must be some protection against positive pressure so that the lung cavity is not subjected to positive pressure. Since the physiologically normal pressure of the pleural space is between −3 and −8 cm of water, any positive pressure within the pleural space is abnormal and can be very dangerous. Finally, the lung cavity must be protected from excessive negative pressure. If the pressure in the lung cavity falls below a predetermined minimum (i.e., excessive sub-atmospheric pressure) lung tissue can be damaged and sutures could become dislodged which could lead to bleeding. A suitable chest drain protects a patient by preventing the reverse flow of air back into the lung cavity within a given range, preventing positive pressure in the lung cavity and preventing excessive sub-atmospheric pressure in the lung cavity.

A one-way valve is used to allow fluid to flow from the chest to the collection device and prevent the reverse flow of air back into the lung. This one-way valve may be mechanical or water-based. When the one-way valve is water-based, it usually takes the form of a U-tube in which water is disposed on the bottom. Such a water-based one-way valve is usually called a water seal. The water seal protects the patient from excessive sub-atmospheric pressure by allowing air pressure to equalize by the flow of air back into the collection chamber (and the lung cavity) if the lung cavity develops excessive sub-atmospheric pressure.

Various persons have suggested the replacement of the water seal with a mechanical one-way valve that would prevent the reverse flow of air back to the patient. The inclusion of a mechanical one-way valve provides advantages because water would not be necessary for the device to operate. However, the inclusion of a mechanical one-way valve has required the incorporation of a specific so-called "negative pressure relief valve" so the patient can be protected from excessive sub-atmospheric pressure. Nearly all typical devices include a positive pressure relief valve that protects a patient from positive pressure.

The design of the one-way valve for use in a chest drainage device poses engineering challenges because the valve should open at a very slight pressure difference between the upstream side and the downstream side of the valve. Additionally, a valve used in a chest drainage system should allow for significant flow of air through the device. The designs must also be cost effective. In an era of cost containment for healthcare, devices that have fewer, simpler parts can be manufactured less expensively than a device with many parts. Accordingly, there is a need for a chest drainage device with fewer working parts that can be inexpensively produced. Additionally, there is a need for a single valve which can perform multiple functions.

BRIEF SUMMARY OF THE INVENTION

A valve according to the present invention includes first and second sealing surfaces that are opposed so that air is allowed to flow from an upstream to a downstream location through the first and second sealing surfaces. Air is prevented from moving from the downstream location to the upstream location when the first and second sealing surfaces are in contact. The valve element allows air to move from the downstream chamber to the upstream chamber when a certain pressure differential is achieved. Specifically, the valve according to one embodiment of the present invention also includes a pressure relief actuating element disposed in the valve and located adjacent the valve element. When a predetermined pressure differential between the upstream side and the downstream side is reached, the valve element deforms and contacts the pressure relief actuating element so that the element causes the first and second sealing surfaces to separate and reduce the pressure differential between the upstream side and the downstream side. The valve according to an embodiment of the invention also includes reinforcing portions along at least a portion of the length of the valve. The reinforcing portions provide additional rigidity to the valve when the pressure in the upstream location is lower than the pressure in the downstream location and allows the sealing elements to be flexible so that the sealing elements open at slight pressure differentials when pressure in the upstream location is higher than the pressure in the downstream location.

One embodiment of the present invention provides a valve for use in a chest drainage device. The chest drainage device is adapted to receive liquid and air from a patient's chest cavity via an inlet and to permit air to escape from the chest drain through an outlet. According to one embodiment, the inlet and outlet define a flow path in which the dual protection valve is disposed along the flow path and includes the following characteristics: a valve element that separates an upstream side (or chamber) from a downstream side (or chamber). The terms upstream and downstream are used to characterize the locations (or spaces) with respect to the valve in typical flow conditions. Under typical conditions the valve operates to allow fluid to flow from the upstream side to the downstream side at very low pressure differentials. That is, a valve according to one aspect of the invention has a very low cracking pressure. Additionally, the valve has a high flow-through capacity so that air can flow through the valve without significant constriction.

A valve constructed according to an embodiment of the invention prevents reverse flow under certain conditions. Specifically, when the pressure difference between the upstream side and downstream side is within a predetermined limit, i.e., the downstream side has a higher pressure than the upstream side, the valve will prevent reverse flow. Accordingly, the valve operates as a one-way valve and opens when the pressure difference between the upstream side and the downstream side is positive and prevents reverse flow when the pressure difference between the upstream and the downstream is negative. In certain conditions the valve will allow the flow from the "downstream" side to the "upstream" side to relieve a pressure difference between the two sides of the valve. Specifically, if the pressure differential between the upstream side and the downstream side is above a predetermined limit, the valve will operate to reduce the pressure difference between the upstream and downstream locations. In such a condition, the valve opens and allows higher pressure air into the upstream chamber so that the pressure is increased to a relieve the pressure in the upstream chamber.

Other aspects of the valve constructed according to the invention are that it may be constructed of silicone and may preferably have a durometer of between 10 and 90 Shore A hardness. A preferred embodiment is constructed with a material having a durometer about 40 Shore A. In another feature, the valve element has a generally circular cross-section. The pressure relief actuating element is located proximate the valve element such that when the air pressure differential between the upstream chamber and the downstream chamber is above a predetermined value, the air in the downstream chamber causes the valve element to deform and contacts the pressure relief actuating element so that the valve sealing surfaces open and cause an increase in the pressure in the upstream chamber (or, said differently, a decrease in the pressure difference between the two chambers). Additionally, the valve may include two generally flat surfaces which taper at the end of the valve element and the first and second sealing surfaces extend along a line formed by the meeting of the two flat surfaces. The valve element may include a flexible flange portion that deforms at a predetermined pressure differential between upstream and downstream sides of the valve. The flat surfaces may be constructed to deform in a manner to contact the pressure relief actuating element so that first and second sealing surfaces at least partially open to allow air into the upstream chamber. The valve may further include a base and a cap and the valve element may include a flange that is at least partially disposed between the base and the cap to secure the valve element.

In another embodiment of the invention, a valve is described that separates an upstream location from a downstream location in a flow path, the valve includes: a valve element with first and second opposed sealing surfaces and a flange having a lower surface. The valve may also include a base member that has a generally circular longitudinal cross-section with a lumen for the passage of air through the base, the base member may also include a surface which is adapted to receive the lower surface of the flange, and the valve element may be secured to the base. A pressure relief actuating element may be disposed on the base and project along a generally axial direction toward the sealing surfaces and adjacent the valve element. The pressure relief actuating element is adapted to open the sealing surfaces when the negative pressure differential between the downstream chamber and the upstream chamber exceeds a predetermined limit to reduce the pressure differential between the chambers.

In this, and other embodiments of the invention, the flange has an upper surface and the valve may further comprise a cap member that has a generally circular longitudinal cross-section with a lumen for the passage of air through the cap, the cap includes a surface which is adapted to receive an upper surface of the flange and the flange may be secured between the base and the cap. The sealing surfaces may also be configured to form a line and, in addition, the valve element may have two generally planar surfaces, perhaps structurally reinforced, that may intersect at a line intersecting the axis of the valve element, wherein sealing surfaces are generally located at the intersection of the planar surfaces. The valve element extends axially from the center of a diaphragm. The valve may include a configuration wherein the pressure relief element is disposed adjacent the flat surfaces and, when the pressure differential between the upstream side and the downstream side exceeds a predetermined value, e.g., the downstream side at 0 cm water gauge and the upstream side at −80 cm water gauge, the diaphragm deforms and the valve element contacts the pressure relief actuating element causing the first and second sealing members to open. Additionally, the base may further include a cylindrical tube with a lumen, wherein the lumen is adapted to be snap-fit into an opening to secure the valve.

Other features of this, and other, embodiment of the invention, include that the valve element may have a generally tapered section and the pressure relief actuation element is located within the a valve element such that when the pressure difference between the upstream chamber and the downstream chamber is above a predetermined pressure, the valve element deforms and contacts the pressure relief actuating element so that the valve sealing surfaces are opened to decrease the pressure difference between the upstream chamber and the downstream chamber. The valve element may have a radially extending diaphragm portion and the pressure difference may cause the diaphragm portion to deform such that sealing surfaces move into contact with and are separated by the pressure relief actuating element. Further, the valve element may include two generally flat surfaces which taper at the end of the valve element and the first and second sealing surfaces extend along a line formed by the intersection of the two flat surfaces. The valve element may be constructed to displace in a manner to contact the pressure relief actuating element such that the first and second sealing surfaces at least partially open to allow air into the upstream chamber. The valve may also include a cap and a portion of the valve is secured between the base and the cap.

BRIEF DESCRIPTION OF THE DRAWINGS

These and other benefits of the present invention will be more easily understood when considered in conjunction with the following illustrations, wherein.

DETAILED DESCRIPTION

The description of the inventive valve is in the context of a chest drainage device. Of course, the valve may be used in other medical and non-medical fields which require similar functionality. As used in this application the term "pressure" refers to gauge pressure, that is ambient air pressure will be at 0.0 cm of water. Pressure above ambient air pressure will be positive and pressures below ambient are negative. Pressure differences are generally referred to as positive pressure differences when going from the upstream side to the downstream side, unless otherwise indicated. That is, a positive pressure difference of, for example, 2 cm of water will open the valve and allow air to flow from the upstream side to the downstream side. A negative pressure difference could occur if the downstream side has a higher pressure than the upstream location. As an example, a downstream pressure of atmospheric pressure and a −8 cm of water pressure in the upstream location would be termed a negative pressure difference.

The fluid recovery system of the present invention provides a housing having a collection chamber for collecting fluid drained from the patient. The housing also contains multiple components, such as valves that are constructed as sub-assemblies and inserted into the housing. In particular, one aspect of the present invention provides for a single valve that provides a one-way flow at certain pressures and operates as a high negativity relief valve, which protects the patient from excessive negative pressure differences. In operation, the valve of the present invention opens to allow air to escape at low positive pressure differentials, e.g., between 0 and +4 cm of water. The valve prevents the flow of air back to the patient during operation so air will not re-enter the pleural cavity. Under certain circumstances, a patient may develop or be exposed to excessive sub-atmospheric pressure, e.g., excessive "negative" (below atmospheric) pressure. When an predetermined pressure limit is reached (e.g., —80 cm H$_2$O), the valve will open to allow reverse flow so that the patient is not exposed to further excessive sub-atmospheric pressure. This combined valve reduces the number of parts for a chest drain and simplifies the construction of the device.

The dual action valve of an embodiment of the present invention optimizes four performance characteristics. The four characteristics are: reverse flow leakage, cracking pressure under positive pressure conditions, negative pressure relief function (both opening and closing) and volumetric air flow capacity. These characteristics are not independent, nor can the analysis of one characteristic exclude the consideration of the others.

Figure 1:
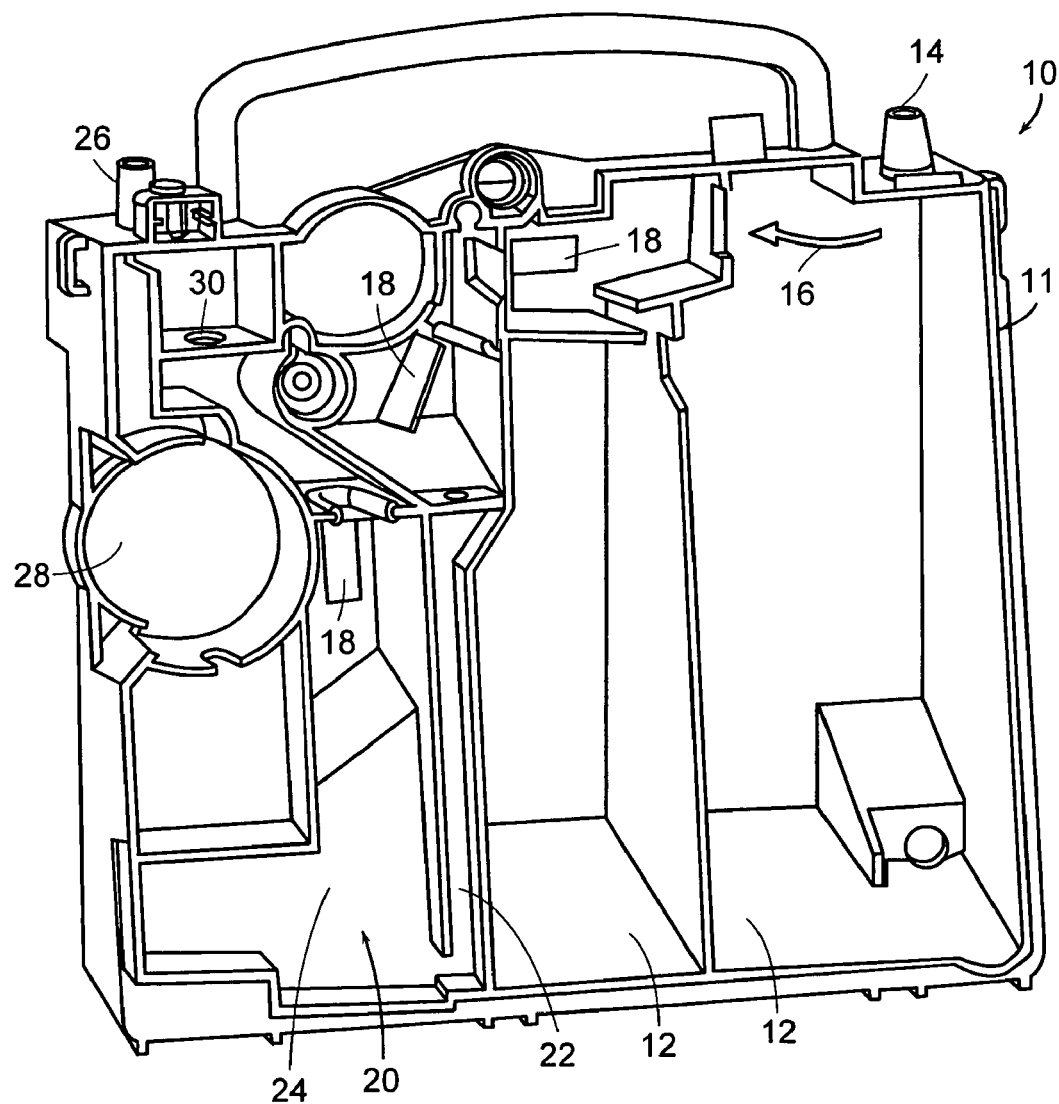
FIG. 1 is a perspective view of a fluid recovery system which is adapted to incorporate an embodiment of the present invention.

With particular reference to FIG. 1, a chest drain 10 includes a housing 11 and a clear front plate (not shown). The front plate is secured to the housing by any suitable techniques, such as vibration welding. The housing includes fluid collection chambers 12 that are adapted to retain fluid (liquid) from a patient. The size of the collection chambers can vary depending on the design of the chest drain, typically the collection chambers retain between 1 liter and 2 liters of liquid. Fluid, both air and liquid, enter the chest drain through an opening 14 which is attached by a flexible tube (not shown) to a patient's chest cavity. The tube can be of any construction that allows for secure, airtight fittings, that will not permit the connection to leak. Liquid that enters the chest drain is collected in the collection chambers, as described above. Air that is drained (removed) from the patient is allowed to enter the chest drain and will follow the path indicated by arrow 16.

The air that is drained (removed) from the pleural space of the patient may have entered by an external puncture of the chest or, perhaps, from a lung that has incompletely healed from surgery and is allowing air to pass from the inside of the lung to the pleural space. The pleural space must be sealed so that the negative pressure is restored because the lung cannot expand properly without the ability to create a negative pressure in the pleural space. Even when the air leak is healed, the presence of fluid in the pleural space will prevent a full expansion of the lungs upon inhalation. The one-way valve prevents the reverse flow of air back into the lungs and makes re-expansion of the lung possible.

Air that enters the chest drain passes through a series of baffles 18. The baffles reduce the possibility that liquid in the collection chamber can spill into other parts of the chest drain. A U-tube 20 with a relatively narrow leg 22 and a relatively wider leg 24 provides an optional water seal/air leak detector. When the U-tube is filled with water, the water allows air to escape through tube 22 and to the "downstream" (away from inlet 14) part of the chest drain. Air will be prevented from flowing backwards by the water "trapped" in the U-tube. Additionally, suction can be applied to the chest using port 26 and is regulated by a suction regulator (not shown) disposed within a compartment 28. These features are more completely described in U.S. Pat. No. 6,358,218, which is incorporated by reference in its entirety.

Downstream from the U-tube is an opening 30 along the flow path. The opening is adapted to fit a valve (illustrated in FIG. 2), according to one embodiment of the present invention, which can be inserted as a "snap-fit" as more completely described below. The valve serves two important functions for the chest drain. First, the valve allows air to pass from the patient and operates to prevent reverse flow back to the patient under normal operation. If the patient generates or is exposed to an excessive amount of sub-atmospheric pressure, the valve also operates to relieve the sub-atmospheric pressure (vacuum) by opening and allowing air to enter the collection chamber. The details of the structure and the function of the valve are described below. With respect to the valve, the upstream location is below the opening 30 and the downstream location is above the opening 30.

Figure 3:
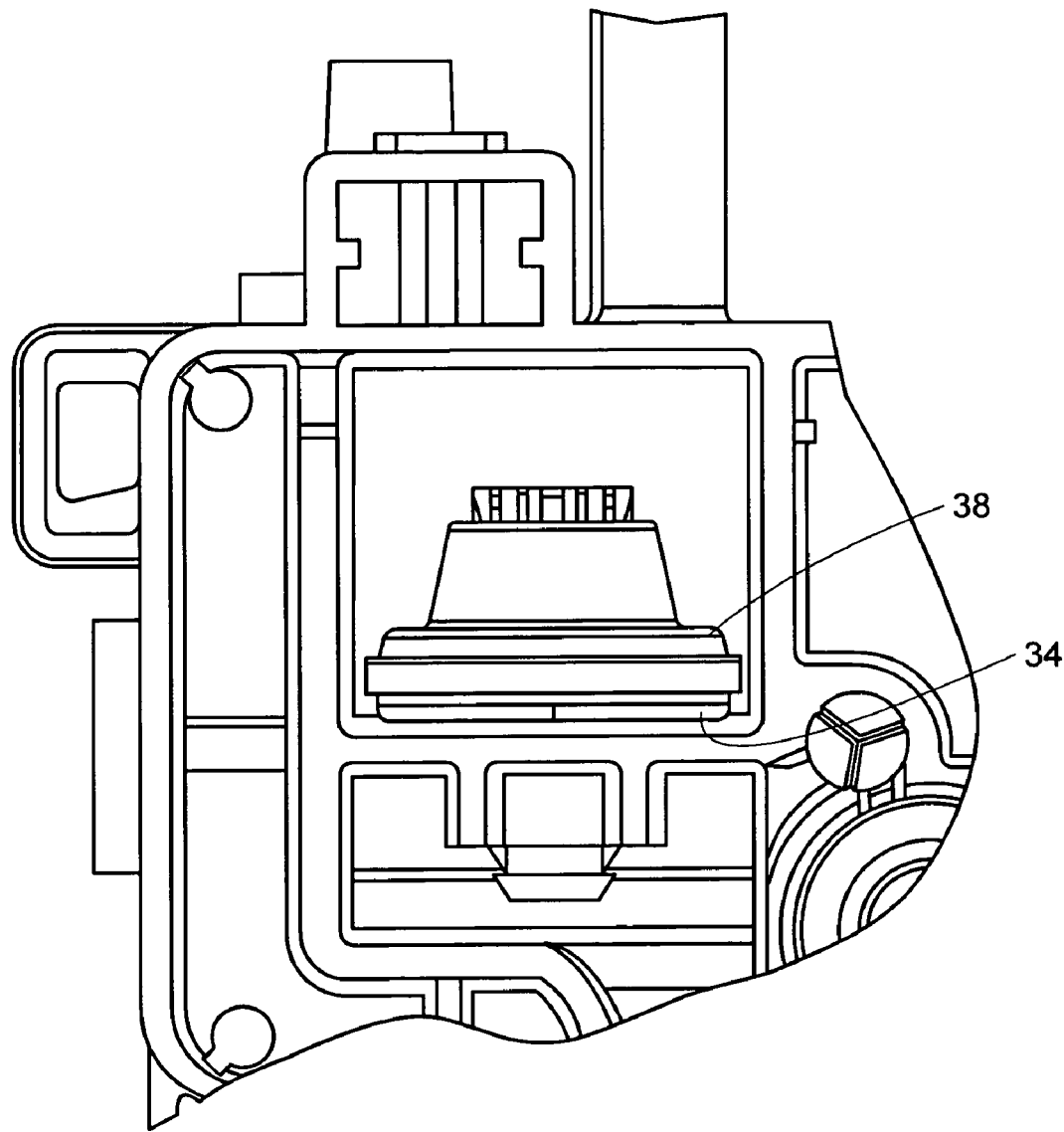
FIG. 3 is a detail view of the dual protection valve as presented in FIG. 1.
Figure 4:
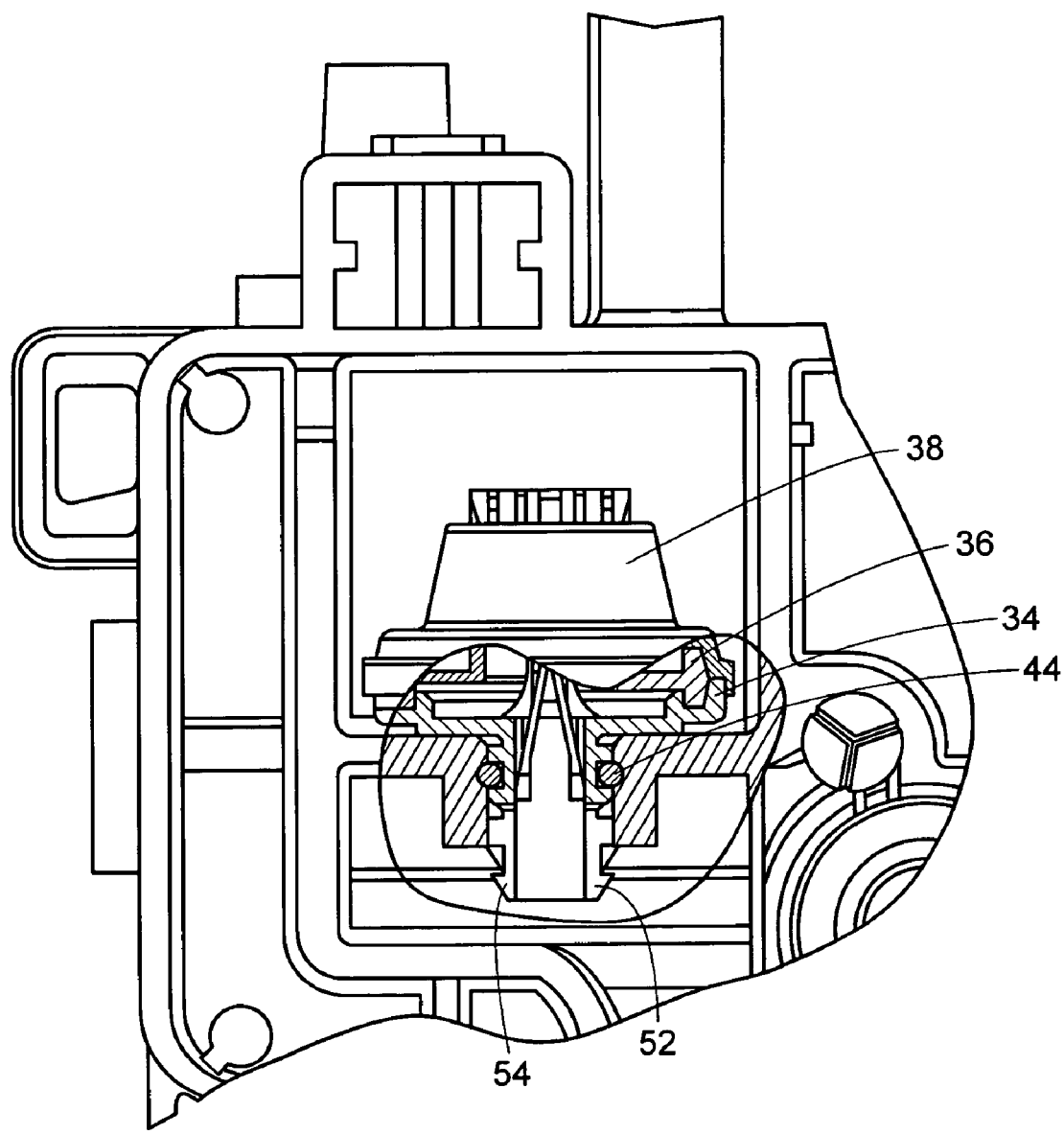
FIG. 4 is a partial cross section of the dual protection valve located in a chest drainage system, such as illustrated in FIG. 1.

The valve according to an embodiment of the application is described with reference to the following Figures, in which like reference numbers refer to like elements. With specific reference to FIGS. 2–4, the dual protection valve 32 includes three components, a base 34, the valve element 36 and the cap 38. The base 34 has a generally circular cross section and includes a cylindrical tube 40 extending from the lower side that cooperates with the opening in the wall of the chest drain so that the dual protection valve can be inserted and secured within the wall along the flow path in the chest drain. The cylindrical tube is rigid and has an outwardly facing groove 42 that is adapted to fit an O-ring 44 which seals the opening so that air only passes through the valve and air cannot pass between the cylindrical tube and the opening. FIG. 4 illustrates the O-ring in the groove. The O-ring is of a typical construction. The cylindrical tube is contoured such that the valve can be inserted into the opening with a snap fit. FIG. 4 illustrates the locking snaps 52, 54 which secure the valve in the housing along the flow path. The insertion is facilitated by two slots 46 (only one of which is illustrated in FIG. 2) which extend longitudinally along the tube 40. The slots allow the relatively rigid cylindrical material to deform sufficiently to allow the locking snaps to pass beyond the housing wall and "snap" into place.

The base 34 has a body that widens above the cylindrical tube that forms a downwardly facing shoulder 56 (shown in FIG. 5) that is spaced from the notches the same distance as the housing wall thickness so the valve is secured to the housing between the shoulder and the notches. Integrally molded with the base is a pressure relief actuating element 58 which is illustrated as a pin that extends axially from the center of the base in a direction toward the cap 38. The pressure relief actuating element 58 is generally rigid and includes reinforcing ribs 62 which extend radially to the upwardly facing surface of the base. The ribs provide lateral support for the pressure relief actuating element while allowing sufficient open cross-sectional area through the base for air to flow through. The tip of the pressure relief actuating element 58 has a smooth, rounded surface. The pressure relief actuating element 58 cooperates with the valve element to provide the negative pressure relief as discussed further below.

Figure 5:
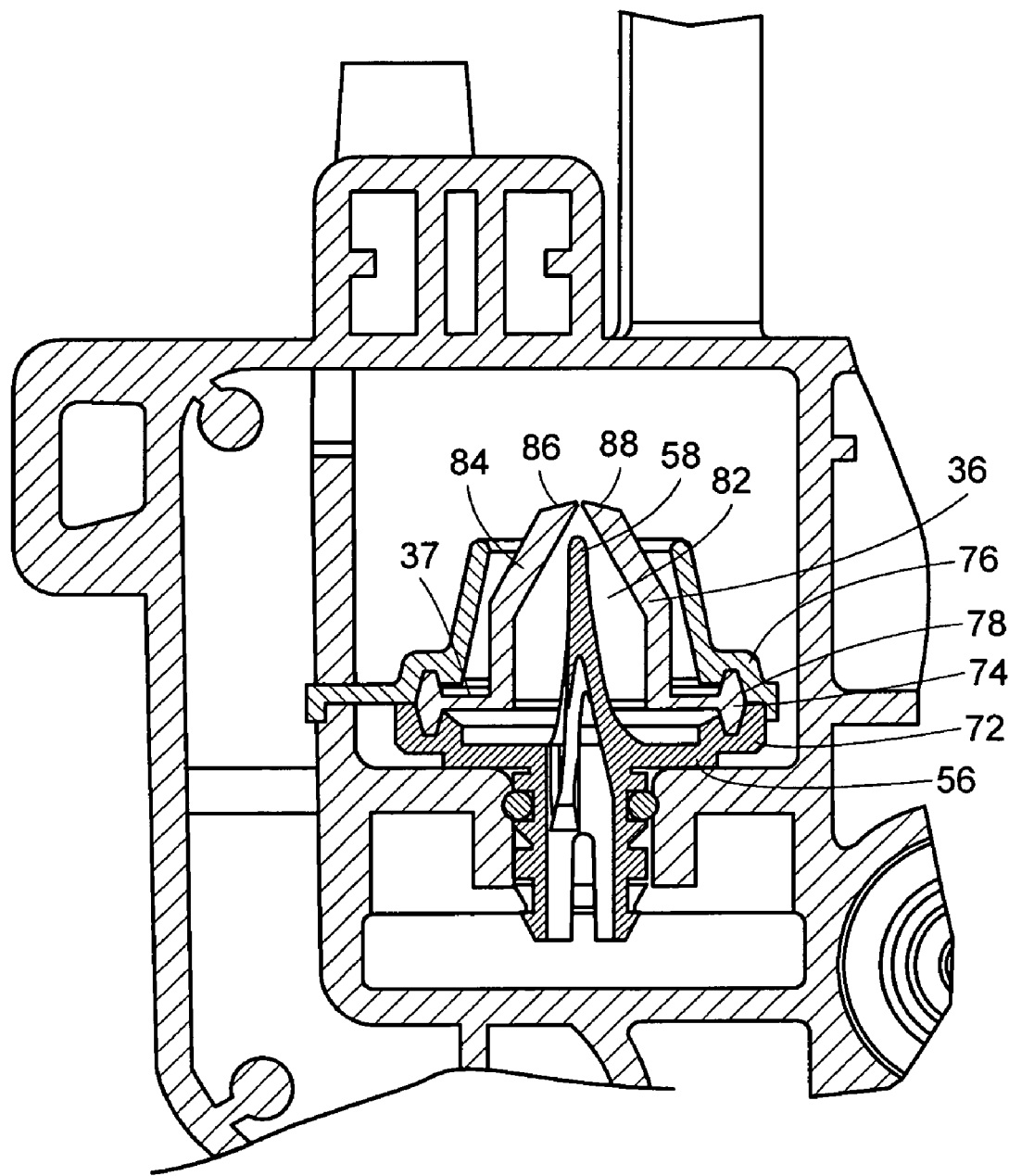
FIG. 5 is a cross section of the dual protection valve located in a chest drainage system.

As FIG. 5 illustrates, the base 34 also includes an upwardly facing annular groove 72 that is sized to receive a cooperating cylindrical portion 74 of the valve element 36. The cap 38, which has a generally circular cross-section downwardly facing annular groove 76 that is sized to receive a cooperating cylindrical portion 78 of the valve element 36.

The valve element 36 has a generally flat diaphragm 37 and a centrally located axial passage 82 through which air can pass; the passage tapers at its upper end. As illustrated, the tapered valve element includes two flat sides or facets 84 reinforced by reinforcing members 85, which are illustrated as ribs in FIG. 2A. In the embodiment described and illustrated, the term "rib" includes all the various structures and materials which could be used to reinforce the valve element, as described in more detail below. Alternatively, the two facets 184 may be comprised of two flat, smooth sides, as illustrated in FIG. 2B.

Figure 2A:
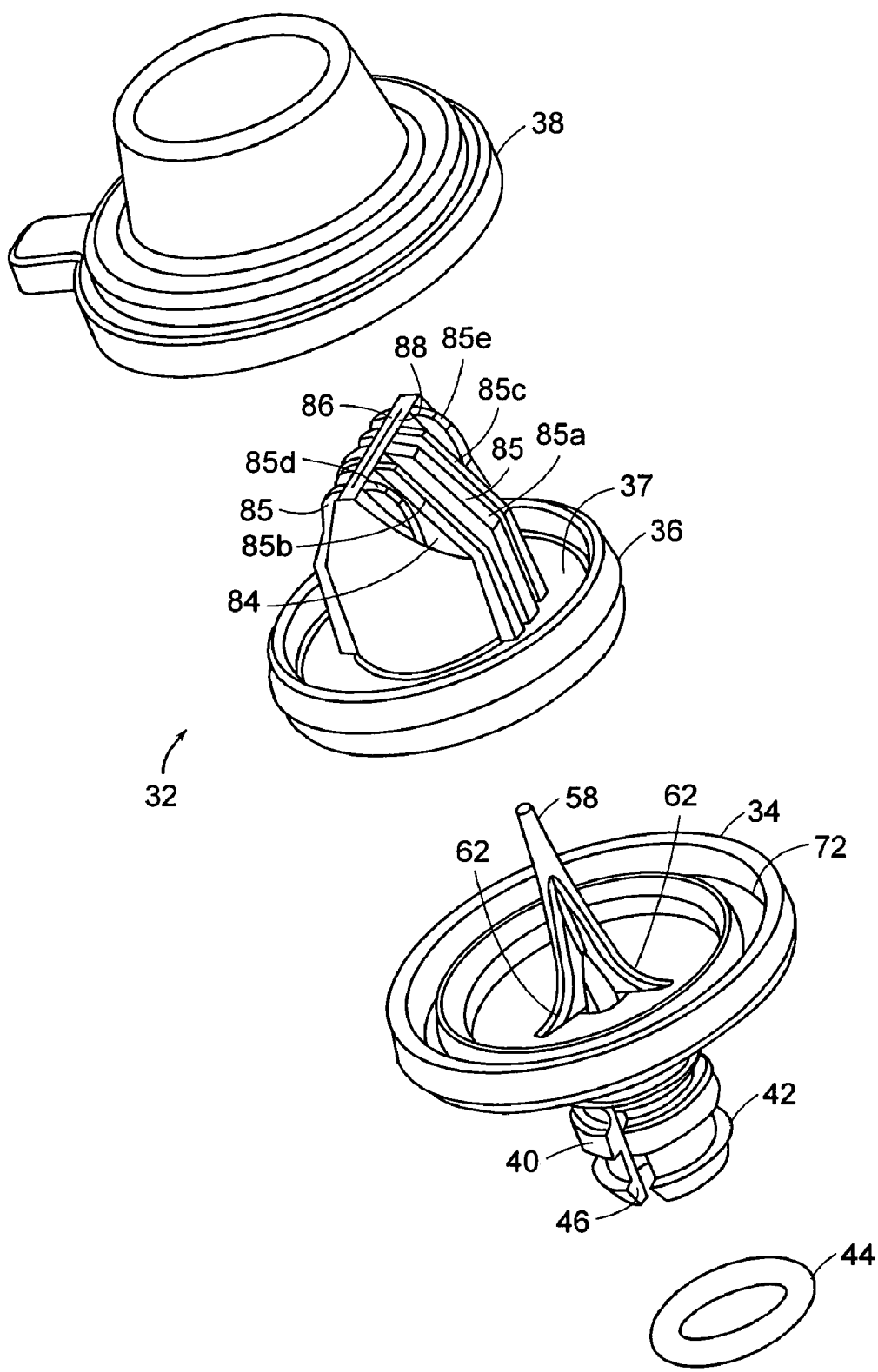
FIGS. 2A and 2B are expanded views of alternative embodiments of the components of the dual protection valve.
Figure 2B:
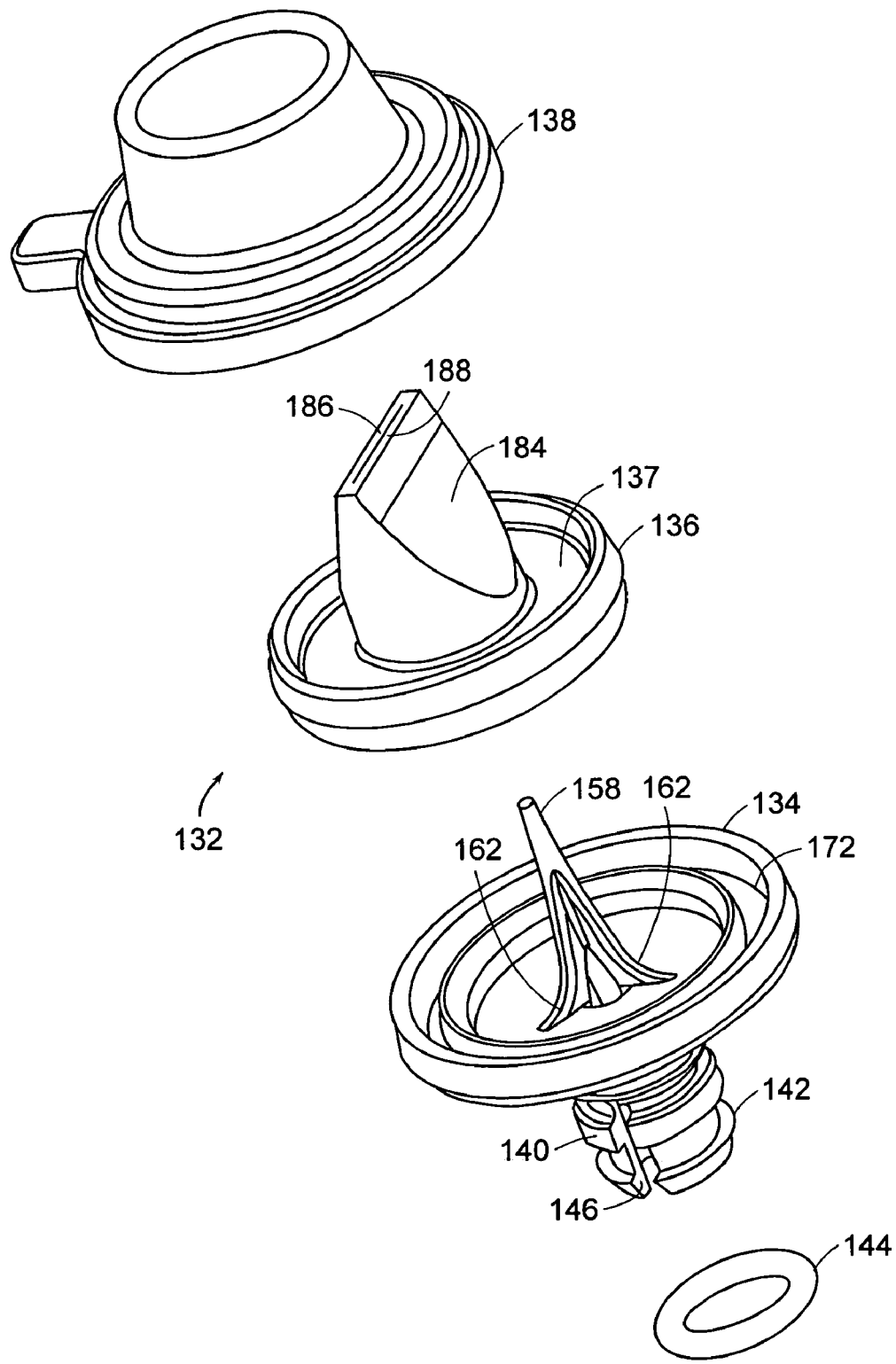

The ribs 85 may extend along the entire length of the valve element as illustrated in FIG. 2A. An individual rib, designated by reference numeral 85a in FIG. 2A may be thicker than other individual ribs, e.g., ribs designated by reference numerals 85b and 85c. The increased width of the rib at the center location assists in providing sufficient stabilizing force for the valve element when subjected to a downward force caused by a high pressure difference between the downstream and the upstream locations. The same effect may be achieved by increasing the thickness of the rib or a combination of the two. The ribs 85b and 85c are disposed at a location where the downward forces are smaller. Similarly, the ribs 85d and 85e are disposed at a location where the forces are smaller still and are not required to be disposed along the entire axial length of the valve element. Accordingly, the ribs of the present invention provide stability for the valve surfaces or faces when there is a downward pressure against the valve element. Because the ribs are separated, the flexibility of the sealing surfaces is maintained and allows the valve to open at small positive pressure differences. That is, the ribs increase the stiffness of the valve element along the longitudinal direction but do not substantially increase the stiffness of the valve element along the line of the sealing surfaces.

In this specific embodiment, the rib 85a has a height and width of 0.050 in. and 0.050 in. Ribs 85b and 85c are separated from rib 85a by a distance of 0.040 in. and have a height and width of 0.040 in. and 0.030 in. Ribs 85d and 85e are separated from ribs 85b and 85c, respectively, by a distance of 0.035 in. and have a height and width of 0.030 in. and 0.030 in. Of course, individual dimensions are illustrative only and the invention may be practiced with more or fewer ribs or without ribs at all.

The valve element sides may be reinforced along the longitudinal length and, although ribs 85 are illustrated, there are other configurations which would achieve the same beneficial effect. For example, longitudinally extending reinforcing members may be embedded in the wall or facet. In this circumstance the exterior of the wall may appear smooth but the wall will be reinforced to allow the valve to open at small differences in pressure and the walls will not collapse when subjected to increased pressure differences, e.g., the downstream pressure becomes higher than the upstream pressure.

The downstream edge of the facets 84 or 184 form a laterally extending line. A slit is formed at the line created by the facets 84 or 184, the slit includes a pair of sealing surfaces 86, 88 or, alternatively, 186, 188. The sealing surfaces are adapted to open when pressure at the lower part (upstream) of the housing is higher than at the upper part (downstream). The pressure at which a valve opens is called the cracking pressure. One of the design constraints of a mechanical one-way valve used within chest drains is that the valve must prevent back flow while at the same time allow for the positive pressure and high flow of air through the valve when an air leak is present. Typically, the valve should allow at least 15 liters per minute, and ideally 30 liters per minute or more, of air flow with a 40 cm of water pressure differential applied between the upstream and downstream side.

The valve element is constructed from silicone and is molded as in integral piece. The material has a hardness of between 30 and 70 (Shore A durometer), with a preferred value of 40. The valve element is manufactured by using standard molding techniques, such as injection molding. The valve sealing surfaces may be created by a slit cut into the distal end of the valve element after the molding process. Alternatively, the slit may be molded into the element. The valve element is constructed to provide the necessary one-way flow control that is desirable for a chest drain and other drainage devices. The sealing surface may extend the entire distance of the line where the two facets meet.

Figure 6:
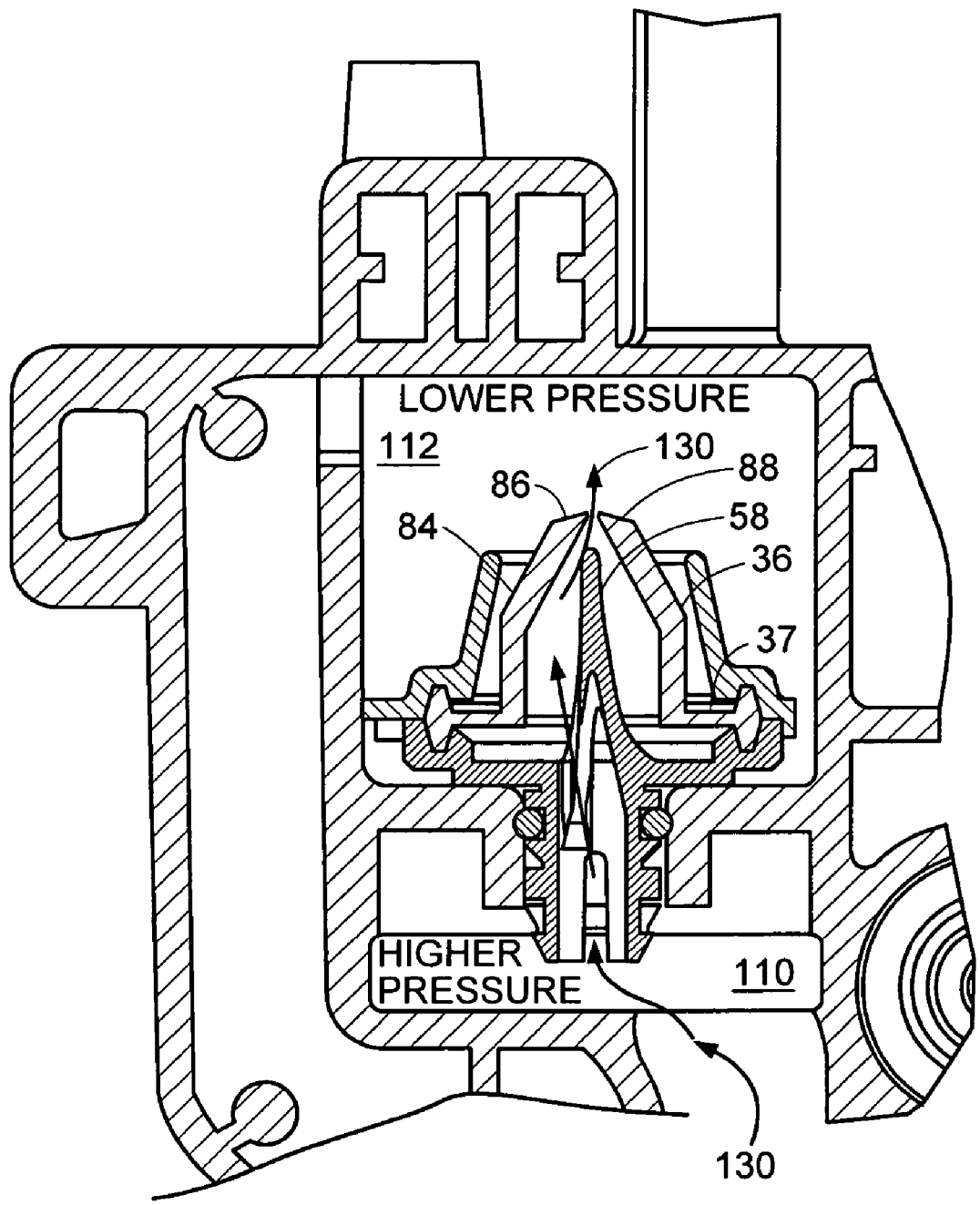
FIG. 6 illustrates the dual protection valve slightly open to allow air to pass from the patient through the chest drain.

FIG. 6 illustrates the vacuum protection valve slightly open to allow air to pass through the valve and escape. The valve element is designed to allow air to flow through the valve at a low differential pressure. Although the pressure (cracking pressure) may vary depending on a variety of conditions, typically it is desirable to have the valve open when the pressure is between 0.0 and +4 cm water. The valve opening, described previously, is adapted to have a sealing surface that extends across the top of the faceted sides. The valve will open as much (or as little) as necessary to relieve the positive pressure differential.

The performance characteristic of volumetric flow capacity is one of the four important characteristics and it may influence the overall design of the valve. Many factors contribute to the overall volumetric flow capacity of a valve, including: flow path geometry of the rigid base and cap, material hardness, wall thickness, geometry, including the diameter of the base and slit width. Many of these features also significantly influence one or more other parameter. Additionally, the valve characteristics can influence the overall volumetric flow rate of a chest drain device.

According to one embodiment, the valve opening desirably will accommodate a flow rate of at least 15 liters per minute under a pressure differential of 40 cm H2O. Optimally, a volumetric flow rate of 30 liters per minute is desired because many clinicians believe this level of flow capacity allows adequate evacuation of air from the thorax in the presence of large air leaks. Of course, geometry of the valve itself and material selection are also significant to the operation of the valve. For example, in one embodiment of the present invention the base diameter of the cylinder required a size of 0.270 inches to deliver the minimum flow capacity when the material in the hardness range of 30–70 Shore A. In another embodiment, the base diameter of the cylinder required a size of 0.400 inches for a flow of 30 liters per minute As illustrated in FIG. 6, the valve element 36 is disposed between upstream chamber 110 and downstream chamber 112. The valve element deforms to allow air represented by arrows 130 to pass through the valve and release any positive pressure above the cracking pressure. The deformability of the valve is important to providing the desired flow rate capacity to the valve and the desired cracking pressure. When ribs (either protruding or internal) are used, the valve maintains a desired (low) cracking pressure due to the orientation of the ribs. That is, since the ribs are oriented in the longitudinal direction, the valve is able to open without the ribs contributing significantly to the stiffness of the valve sealing surfaces that influences the cracking pressure of the valve.

The valve according to the present invention also protects the patient from excessive pressure differences between the upstream and downstream sides, e.g., when the upstream side has excessive sub-atmospheric pressure. Under certain operating conditions, the cooperation between the pressure relief actuating element 58 and valve 36 causes the valve to open such that air will flow back and relieve the excessive low pressure in the collection chamber (and thus in the patient's lung cavity). The operation of the valve when the downstream pressure is higher then the upstream pressure is described in connection with FIGS. 7 and 8. As in FIG. 6, the valve element of FIGS. 7 and 8 separates the upstream chamber 110 from the downstream chamber 112. The downstream chamber is connected to the fluid collection chambers and, ultimately, to the patient. If the patient experiences excessive sub-atmospheric pressure, the pressure in the downstream chamber will be greater than the pressure in the upstream chamber. The force of excessive pressure difference (in excess of a predetermined amount) will press against the valve diaphragm. Specifically, the pressure in the downstream location will press against the diaphragm and push the valve element toward the relief actuation element.

The valve is designed to function as a one-way valve and will not open to relieve pressure until the pressure difference between the upstream chamber and the downstream chamber reaches a predetermined value. The valve of the present invention is designed to prevent the reverse flow of air under the pressure conditions below the predetermined value. For example, in a typical situation where a chest drain is attached to a patient, the pressure in the downstream chamber may be at atmospheric pressure (because it may open to the atmosphere) and the upstream pressure is –2 to –8 cm of water (because the patient may be healing). Under these operating conditions the valve will prevent the reverse flow of air. This is desirable because it will allow the patient to develop the appropriate sub-atmospheric pressure without allowing any air to flow back and possibly cause air to enter the pleural space.

Figure 7:
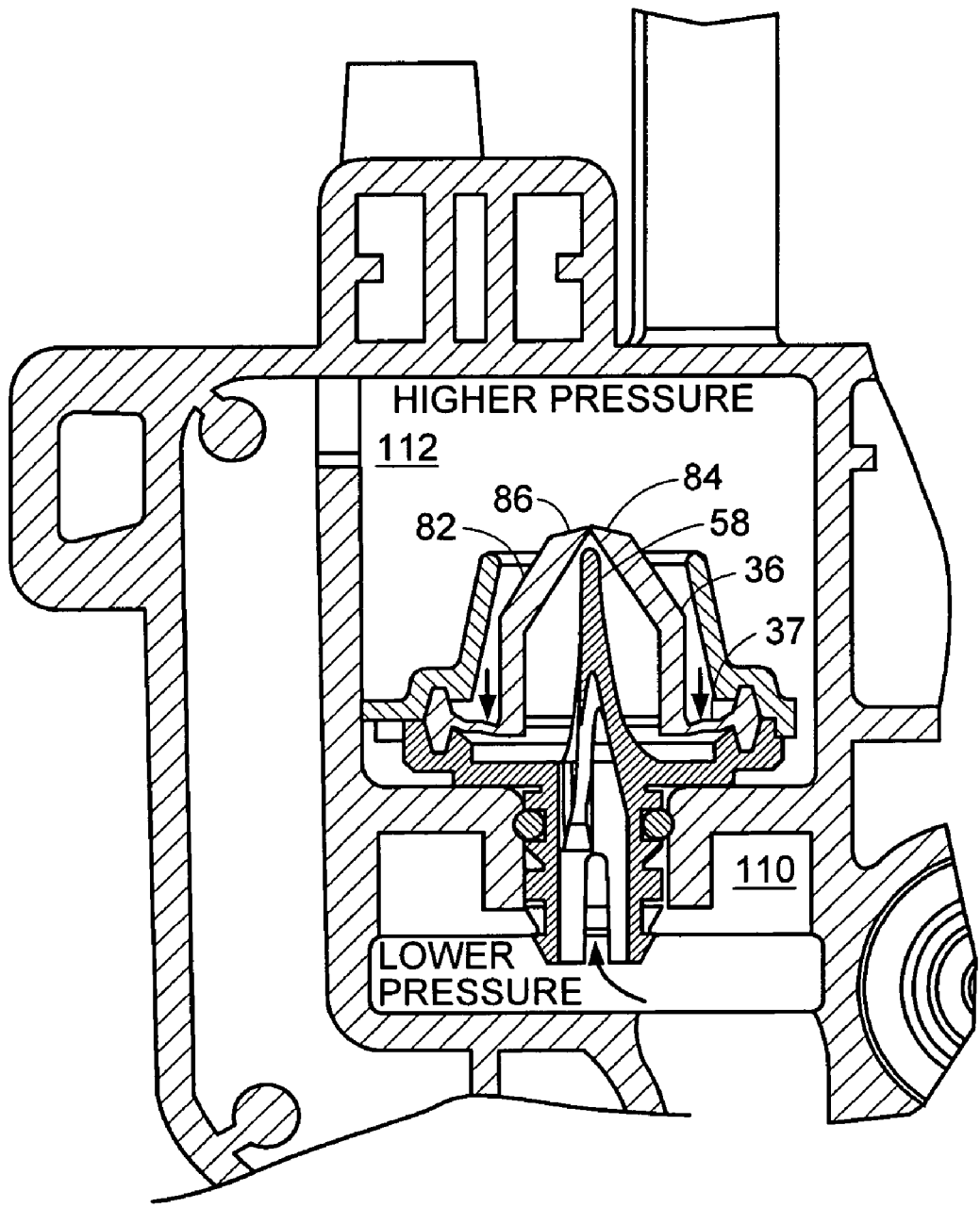
FIGS. 7–8 illustrate the dual protection valve at various positions when sub-atmospheric pressure is present in the chest cavity.

As illustrated in FIG. 7, the valve element 36 has deformed slightly in response to a pressure differential between the upstream chamber 110 and the downstream chamber 112. As readily apparent from the illustration, the diaphragm 37 deforms slightly toward the side with the lower pressure. Arrows indicate the force applied to the diaphragm. The slight deformation moves the valve seat 86, 88 of the valve element 36 closer to the pressure relief actuating element 58. In the preferred embodiment, the valve does not touch the pressure relief actuating element when the valve element is deformed slightly.

As the pressure difference between the chambers increases, that is, e.g., the pressure in the lower upstream chamber decreases, the valve element moves closer to the pressure relief actuating element 58. When the pressure difference reaches a predetermined value the pressure relief actuating element operates to open the valve seal to allow air from the higher-pressure chamber to the lower-pressure chamber. This is advantageous because if the sub-atmospheric pressure in the upstream chamber (ultimately connected to the patient's pleural space) is exposed to an excessive sub-atmospheric pressure the patient may be adversely affected. Regardless of the source, excessive sub atmospheric pressure will be relieved by the operation of the valve.

Figure 8:
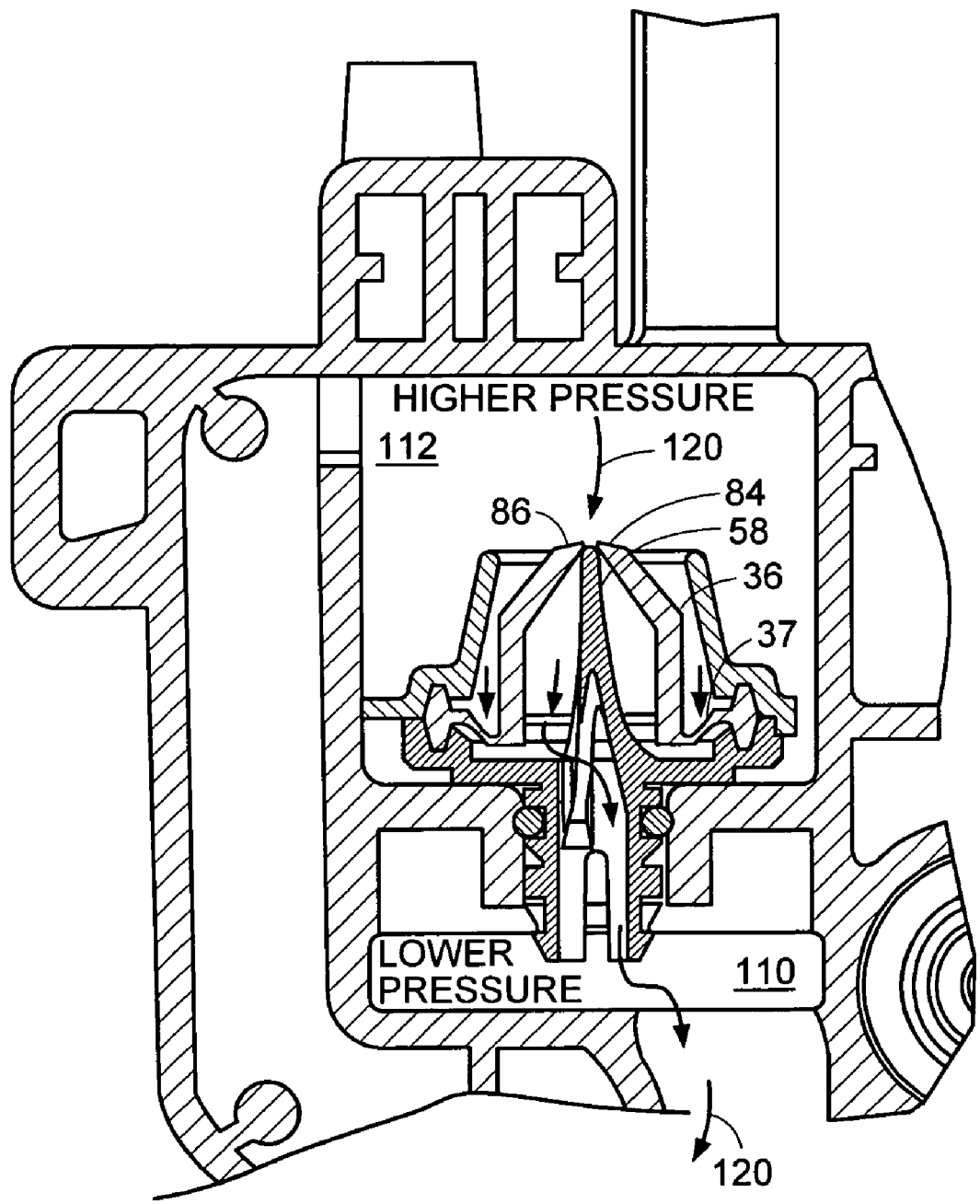

As illustrated in FIG. 8, the pressure difference has reached the predetermined value and the pressure relief actuating element 58 opens the valve seat 86, 88 to allow air to pass into the upstream chamber as represented by arrows 120. In a preferred embodiment the valve opens at a pressure difference of –50 cm of water, although relief pressure differences in the range of –30 to –100 cm of water may be used depending on the design of the system.

As one skilled in the art would understand, the operating pressure of the valve should be designed according to the needs of the entire chest drainage system. That is, there are fluid dynamics that will affect the openings of the valve. Specifically, if the airleak detector is filled with water, the pressure required to "push" air through the system will be the sum of the cracking pressure and the level of water (head) in the tube. Accordingly, it is desirable to design a valve with a low cracking pressure.

Having described various embodiments of the invention, it should be apparent that various combinations of the embodiments may be made or modifications added thereto without departing from the spirit and scope of the invention, which is defined in the claims below.

What is claimed is:

1. A valve for use in a chest drainage device including an upstream chamber and a downstream chamber, said upstream chamber and downstream chamber defining an air flow path, said valve disposed along the flow path, said chest drainage device comprising:

an inlet to the chest drainage device adapted to receive liquid and air from a patient, a liquid collection chamber for collecting liquid, a valve element separating the upstream chamber from the downstream chamber secured to a wall defining the flowpath and having a first and a second sealing surface that are opposed so that, when the first and second sealing surfaces are in contact, air will be prevented from moving from the downstream chamber to the upstream chamber, and when the upstream chamber is at a higher pressure than the downstream chamber, the sealing surfaces will separate allowing air to move from the upstream chamber toward the downstream chamber, and, a pressure relief actuating element located adjacent the valve element such that, when the downstream chamber is at a higher pressure than the upstream chamber and a pressure difference between the two chambers is above predetermined differential value, the valve element deforms and contacts the pressure relief actuating element so that the pressure relief actuating element causes the first and second sealing surfaces to separate.

2. The valve recited in claim 1, wherein the valve element includes two generally planar surfaces, and the first and second sealing surfaces extend along a line formed by the intersection of the two planar surfaces.

3. The valve recited in claim 2, wherein the planar surfaces have reinforcement elements for support.

4. The valve recited in claim 1, wherein the valve element includes two facets and the first and second sealing surfaces extend along a line formed by the intersection of the two facets and further comprising structural reinforcement elements that protrude from the planar surfaces.

5. The dual protection valve recited in claim 4, wherein the reinforcement elements are generally perpendicular to the line formed by the intersection of the two sealing surfaces.

6. A valve for use in a device including an upstream chamber and a downstream chamber, said upstream chamber and downstream chamber defining a flow path, said valve disposed along the flow path, said chest drainage device comprising:

a valve element separating the upstream chamber from the downstream chamber and having a first and a second sealing surface that are opposed so that, when the first and second sealing surfaces are in contact, air will be prevented from moving from the downstream chamber to the upstream chamber, and when the upstream chamber is at a higher pressure than the downstream chamber, the sealing surfaces will separate allowing air to move from the upstream chamber toward the downstream chamber, and, a pressure relief actuating element located adjacent the valve element such that, when the downstream chamber is at a higher pressure than the upstream chamber and a pressure difference between the two chambers is above predetermined differential value, the valve element deforms and contacts the pressure relief actuating element so that the pressure relief actuating element causes the first and second sealing surfaces to separate, wherein the valve element includes two facets and the first and second sealing surfaces extend along a line formed by the intersection of the two facets and further comprising structural reinforcement elements that protrude from the planar surfaces, wherein each reinforcement element that protrudes from the planar surfaces has a width and the width varies among different reinforcement elements.

7. The valve recited in claim 6 wherein the facets have a longitudinal distance and the reinforcement element at the location of the longest longitudinal distance has the greatest width.

8. A valve for use in a device including an upstream chamber and a downstream chamber, said upstream chamber and downstream chamber defining a flow path, said valve disposed along the flow path, said chest drainage device comprising:

a valve element separating the upstream chamber from the downstream chamber and having a first and a second sealing surface that are opposed so that, when the first and second sealing surfaces are in contact, air will be prevented from moving from the downstream chamber to the upstream chamber, and when the upstream chamber is at a higher pressure than the downstream chamber, the sealing surfaces will separate allowing air to move from the upstream chamber toward the downstream chamber, and, a pressure relief actuating element located adjacent the valve element such that, when the downstream chamber is at a higher pressure than the upstream chamber and a pressure difference between the two chambers is above predetermined differential value, the valve element deforms and contacts the pressure relief actuating element so that the pressure relief actuating element causes the first and second sealing surfaces to separate, further comprising a diaphragm that is constructed to deform in a manner such that the valve element contacts the pressure relief actuating element when the predetermined pressure differential value is achieved, causing the first and second sealing surfaces to at least partially open to allow air into the upstream chamber.

9. A valve separating an upstream side from a downstream side in a flow path, said valve comprising:

a valve element which includes a first and second opposed sealing surfaces, the valve element also including a diaphragm having a first surface, and a periphery that generally forms a flange, a base member having a generally circular longitudinal cross-section with a lumen for the passage of air through the base, and, a pressure relief actuating element disposed on the base and projecting in an axial direction toward the sealing surfaces and adjacent the valve element, wherein the pressure relief actuating element opens the sealing surfaces when the pressure in the upstream side is lower than the pressure downstream side and the pressure difference between the sides exceeds a predetermined limit.

10. The valve recited in claim 8 wherein the valve further comprises:

a cap member having a generally circular longitudinal cross-section with a lumen for the passage of air through the cap, the cap and the base being configured to secure the valve element.

11. The valve recited in claim 9, wherein the sealing surfaces generally form a line.

12. The valve recited in claim 9, wherein the valve element has two generally planar surfaces that intersect at a line perpendicular to the axis of the valve element, and the sealing surfaces are generally located at the intersection of the planar surfaces.

13. The valve recited in claim 9, wherein the two generally planar surfaces have reinforcing members.

14. The valve recited in claim 13, wherein the reinforcing members are generally perpendicular to a line created by the sealing surfaces.

15. The valve recited in claim 14 wherein each reinforcing member has a width and the width of the reinforcing members varies.

16. The valve recited in claim 12, wherein the pressure relief actuating element is disposed adjacent the planar surfaces and, when the pressure on the downstream side is higher than the pressure on the upstream side and the pressure difference between the sides exceeds the predetermined limit, the valve element deforms and contacts the pressure relief actuating element causing the first and second sealing members to open.

17. The valve recited in claim 16, wherein the reinforcing members are generally perpendicular to a line created by the sealing surfaces and wherein each reinforcing member has a width and the width of the reinforcing members varies.

18. A chest drainage device for draining fluids from the chest, the chest drainage device comprising an inlet, an outlet, a liquid collection chamber for collecting liquid and an air flow path for air between the inlet and outlet, the air flow path including an upstream side located toward the inlet and a downstream side located toward the outlet,
   a valve element disposed at a location along the air flow path adapted to prevent air flow from the downstream side toward the upstream side and having a first and a second sealing surface that are opposed so that, when the first and second sealing surfaces are in contact, air will be prevented from moving from the downstream side to the upstream side, and when the upstream side is at a higher pressure than the downstream side, the sealing surfaces will separate allowing air to move from the upstream side to the downstream side, where the valve element is secured to a wall defining the flow path, and
   a pressure relief actuating element disposed proximate to the sealing surfaces such that, when the downstream side is at a higher pressure than the upstream side and the pressure difference between the two sides exceeds a predetermined value, the valve element contacts the pressure relief actuating element such that the first and second sealing surfaces separate to decrease the pressure difference between the downstream side and the upstream side.

19. The chest drainage device recited in claim 18, wherein the valve element has a generally tapered section and the pressure relief actuating element is located at an axially central location.

20. A chest drainage device for draining fluids from the chest, the chest drainage device comprising an inlet, an outlet, a fluid collection chamber for collecting fluid and a flow path for air between the inlet and outlet, the fluid flow path including an upstream side located toward the inlet and a downstream side located toward the outlet,
   a valve element disposed at a location along the flow path adapted to prevent fluid air flow from the downstream side toward the upstream side and having a first and a second sealing surface that are opposed so that, when the first and second sealing surfaces are in contact, air will be prevented from moving from the downstream side to the upstream side, and when the upstream side is at a higher pressure than the downstream side, the sealing surfaces will separate allowing air to move from the upstream side to the downstream side, and
   a pressure relief actuating element disposed proximate to the sealing surfaces such that, when the downstream side is at a higher pressure than the upstream side and the pressure difference between the two sides exceeds a predetermined value, the valve element contacts the pressure relief actuating element such that the first and second sealing surfaces separate to decrease the pressure difference between the downstream side and the upstream side,
   wherein the valve element has a radially extending diaphragm portion and, when the downstream side is at a higher pressure than the upstream side and the pressure difference between the two sides equals a predetermined value, the pressure difference causes the diaphragm portion to deform such that sealing surfaces are separated by the pressure relief actuating element.

21. The chest drainage device recited in claim 18, wherein the valve element includes two surfaces which taper towards the sealing surfaces, and the first and second sealing surfaces extend along a line formed by the intersection of the two surfaces.

22. The chest drainage device recited in claim 18, wherein the valve element surfaces are generally flat.

23. The chest drainage device recited in claim 18, wherein the valve element surfaces have reinforcing members to increase the stiffness of the valve element along a longitudinal direction.

24. The chest drainage device recited in claim 23, wherein the reinforcing members are generally perpendicular to the line formed by the intersection of the two surfaces.

25. The chest drainage device recited in claim 23 wherein the reinforcing members do not substantially increase the force required to open the valve when the pressure is higher in the upstream location than the downstream location.

26. The chest drainage device recited in claim 18, wherein the valve element is constructed to displace in a manner to contact the pressure relief actuating element when the downstream side is at a higher pressure than the upstream side, and the pressure difference between the two sides equaling a predetermined pressure differential value, such that first and second sealing surfaces at least partially open to allow air into the upstream chamber.

27. A valve that is adapted to be disposed along a flow path from a region upstream of the valve to a region downstream of the valve, the valve comprising
   a valve element which is adapted to allow flow from an upstream location to a downstream location during conditions of positive relative pressure, said positive relative pressure condition being when the upstream pressure is relatively higher than downstream pressure, the valve element further adapted to prevent flow from the region downstream to a region upstream under a predetermined range of conditions of negative relative pressures, said negative relative pressure conditions being when the upstream pressure is relatively lower than downstream pressure, and,
   a pressure relief actuating element disposed on the valve proximate the valve element such that the valve element does not contact the pressure relief actuating element when the negative relative pressure does not exceed a predetermined limit, and wherein the valve element and the pressure relief actuating element contact when the negative relative pressure exceeds the predetermined limit such that the valve element allows flow to pass from the downstream side to the upstream side,
   wherein the valve element includes a diaphragm that deforms and causes the valve element to contact the pressure relief actuating element and allow flow from the downstream side to the upstream side when the negative relative pressure exceeds the predetermined limit.

28. The valve of claim 27 wherein the pressure relief actuating element is disposed along an axial direction and the diaphragm is disposed along a position transverse the axial direction.

29. The valve of claim 27, wherein the predetermined limit is between −30 and −100 cm of water.

30. The valve of claim 27 wherein the valve allows a flow rate of at least 15 liters per minute at a positive pressure differential of 40 cm of water.

31. The valve of claim 27 wherein the valve element includes tapered sides and a valve seal is formed at the intersection of the tapered sides.

32. The valve of claim 26 further comprising a cap and a base, and wherein the valve element is disposed between the cap and the base.

33. The valve of claim 32 wherein the valve element sides have reinforcing members disposed along a longitudinal direction.

34. The valve of claim 33 wherein the reinforcing members have a width and the width of the reinforcing members varies.

* * * * *